United States Patent [19]

Shattock et al.

[11] Patent Number: 4,619,896

[45] Date of Patent: Oct. 28, 1986

[54] PROCESS FOR OBTAINING DELTA ANTIGEN OF HEPATITIS D VIRUS AND USE OF SAID ANTIGEN AS A DIAGNOSTIC AGENT

[76] Inventors: Alan G. Shattock, Hillside, Bohernabreena, County Dublin, Ireland; Bridget M. Morgan, 123 Plumstead High Street, Plumstead, London SE18 1SE, England

[21] Appl. No.: 580,660

[22] Filed: Feb. 16, 1984

[30] Foreign Application Priority Data

Mar. 4, 1983 [IE] Ireland .................................. 473/83
Oct. 25, 1983 [IE] Ireland ................................ 2499/83

[51] Int. Cl.$^4$ .................. G01N 33/53; G01N 33/544; G01N 33/531
[52] U.S. Cl. ........................................ 435/7; 435/805; 435/810; 436/528; 436/529; 436/530; 436/543; 436/804; 436/807; 436/808; 436/809; 436/810; 436/811; 436/820; 436/825; 436/826
[58] Field of Search ...................... 435/7, 4, 805, 810; 436/528-530, 543, 804, 811, 820, 807-810, 825, 826

[56] References Cited

FOREIGN PATENT DOCUMENTS 3116882  1/1982  Fed. Rep. of Germany .

OTHER PUBLICATIONS

Bonino et al, Infection and Immunity, 43 (1984) 1000–5.
Marion et al, Proc. Nat'l. Acad. Sci. USA 77 (1980) 2941–5.
Rizzetto et al, J. Immunol. 125 (1980) 318–24.
Rizzetto et al, Lancet vol. II (1979) #8150, pp. 986–990.
Imedile et al, Lancet, vol. II (1982) #8305, pp. 945–947.
Rizzetto et al, J. Infec. Dis. 141 (1980) 590–602.
Raimondo et al, Br. Med. J. 286 (1983) 845.
Rizzetto et al, Proc. Natl. Acad. Sci. USA, 77 (1980) 6124–8.
Rizzetto, "Hepatology", vol. 3, No. 5, pp. 729–737 (1983).
Shattock et al, "Journal of Medical Virology", vol. 13, pp. 73–82 (1984).
Govindarajan et al, "Journal of Medical Virology", vol. 14, pp. 33–37 (1984).
Shattock et al, "British Medical Journal", vol. 290, pp. 1377–1380 (1985).

Primary Examiner—Christine M. Nucker

[57] ABSTRACT

A process for 'unmasking' delta antigen in the blood of an animal, known or caused to be infected with the antigen. The process involves treating serum from the animal with a surfactant and optionally with an antibody—antigen dissociating agent. The blood derived delta antigen is used as a diagnostic agent in the detection and determination of different classes of antibodies to hepatitis D. virus (delta agent) by enzyme-immunoassay and radio-immunoassay.

41 Claims, No Drawings

PROCESS FOR OBTAINING DELTA ANTIGEN OF HEPATITIS D VIRUS AND USE OF SAID ANTIGEN AS A DIAGNOSTIC AGENT

BACKGROUND OF THE INVENTION

1. Field of the Invention

This invention relates to diagnostically useful agents, a process for their preparation and their use in diagnostic methods. More particularly, the invention relates to blood-derived delta hepatitis antigen and to its use in the determination and detection of anti-delta antibodies.

2. Description of the Prior Art

The hepatitis agent named delta (δ) was first detected by Rizzetto, M. et al using the technique of immunofluorescence in the liver of some patients chronically infected with the hepatitis B virus or with chronic hepatitis B surface antigenaemia (Gut, 1977 18 997–1003). The delta agent (now called hepatitis D virus) has been shown to be associated with, but not part of, the hepatitis B virus. It is hypothesized that the delta agent is dependent on hepatitis B virus for replication because it has not been reported so far in the absence of markers of hepatitis B virus. It has been held that the agent has a putative genome and that it cannot replicate without the help of hepatitis B virus (Rizzetto, M. et al The Journal of Infectious Diseases Vol. 141, No. 5 May 1980). This hypothesis therefore includes the possibility that constituents of the hepatitis B virus or its associated particles and tubules may also be constituent parts of the delta agent. Evidence in support of this hypothesis includes the finding that antibody to the hepatitis B surface antigen (HBsAg) agglutinates particles found in delta-rich cesium chloride density-gradient fractions (Rizzetto, M. et al Proc. Natl. Acad. Sci. U.S.A. Vol. 77, No. 10 pp. 6124–6128, October 1980). Such particles were not agglutinated by antibody to the delta agent.

Evidence that the delta agent is a virus or virus-like entity is based on transmission experiments to chimpanzees and the demonstration of low molecular-weight RNA in semipurified delta enriched cesium-chloride density gradient fractions (Rizzetto, M. et al Proc. Natl. Acad. Sci. U.S.A supra).

It is likely that the delta agent particles have a structure which can be depicted schematically as follows:

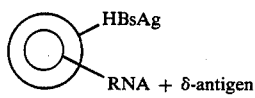

The delta antigen is considered to be a protein and appears to have a molecular weight of 68,000.

It is postulated that delta antigen exists in the blood as part of the particle depicted above and as free delta antigen, some of which may be bound to plasma proteins. The infection that is attributed to the delta agent is commonly associated with persons who illicitly abuse drugs by injection. Delta infection is also reported in persons who receive quantities of blood-derived material, and examples of such persons are haemophiliacs.

Since 1980 delta infection has become very common in Ireland among persons who illicitly abuse drugs by injection (Shattock, A. G. et al Irish Journal of Medical Science, Vol. 151, No. 11, 334–338, 1982). Delta infection appears to be almost worldwide and is even found in isolated South American tribes.

Delta infection is reported to be particularly common in Italy even in those not using illicit drugs or receiving blood-derived products. However, such persons carry or are infected with hepatitis B virus or carry hepatitis B markers. Many of these persons are reported to have chronic forms of hepatitis and although it has not been proved, the implication is that the delta agent may be contributory in some way to the acquisition or maintenance of this chronic hepatitis.

Even more alarming are reports of a higher incidence of delta markers in persons with severe or fulminant forms of hepatitis compared with those with benign hepatitis (Smedile, A. et al The Lancet, October 30, 1982 pp. 945–947 and Raimondo, G. et al Brit. Med. J. 286 p845, March, 1983). This has not been proved but the implication is that delta infection is causative of or contributory to the severe and/or fulminant form of hepatitis. It will be appreciated, however, that the whole picture is complicated by the presence of hepatitis B virus.

The Italian subjects referred to above were deemed to have the delta infection because either they were found to have a marker called the delta antigen in their liver by immunofluorescence, or because they were found to have antibody to the delta antigen (anti-delta) in their blood by radio-immunoassay or enzyme-immunoassay techniques. In the latter studies the delta antigen was derived from liver of a patient with chronic delta infection by extraction of hepatocyte nuclei (disrupted by sonication) with 6M guanidine hydrochloride followed by dialysis and boiling of the concentrated dialysate (Rizzetto, M. et al 1979 The Lancet ii 986–990). By any standards the latter extraction method is severe and may result in antigenic alteration.

German Patent Publication DE-A-3116882 relates to a stable form of the delta antigen of Hepatitis B virus without interfering material and associated liver tissue, a method of isolating the delta antigen from liver and its use as a diagnostic agent for detecting corresponding antibodies indicative of associated disease. It is stated (page 7) that "At present, the human liver which contains delta antigen is the only practical source of the antigen".

A paper by Redeker A. G. in April 1983 (Annals of Internal Medicine Volume 98 No.4) shows that to date serum has not been considered a practical source of delta antigen, since detection of delta antigen serum has only been shown in chimpanzee transmission studies and in a few patients in whom delta antigenaemia has been transiently recorded early in acute delta hepatitis. By transient is meant a few days.

The presence of delta antigen in blood of chimpanzees experimentally infected with delta antigen has been demonstrated after treatment of the serum with various concentrations of the detergent known as Nonidet P40, a non-ionic detergent (Rizzetto, M. et al, 1980; Proc. Natl, Acad. Sci. U.S.A. supra). Delta antigen activity was found to be optimal at a final concentration of 0.3%. Since detection of delta antigen required detergent treatment Rizzetto et al deduced that the delta antigen was an internal component of a discrete subpopulation of HBsAg particles.

Because of this apparently rare and transient presence of the delta antigen in the blood of infected persons, blood has not heretofore been considered as a source of antigen in a technique for the detection of anti-delta antibodies.

Delta antigen is considered to be highly immunogenic since antibody thereto appears very rapidly in the plasma of infected subjects. Since one obtains a negative result for delta antigen with anti-delta antibody within a few days of the first appearance of delta antigen, it has been assumed that delta antigen has disappeared. However, it is now postulated by the Applicants that, in fact, the delta antigen may persist in the bloodstream but bound to delta antibody.

To date, the detection of anti-delta antibodies in blood has been carried out with delta antigen derived from human post-mortem liver. The techniques used for the extraction of the delta antigen from liver are not routine to many laboratories and in any case suitable human postmortem liver is very difficult to obtain and potentially hazardous to the surgeon and handlers who risk infection during the extraction process. As a result, few laboratories have been able to carry out research on the incidence and significance of delta infection simply because they lack a laboratory technique for the detection of delta antigen and anti-delta antibodies.

Liver derived delta antigen is in short supply and, therefore, few laboratories have access to suitable reagents for monitoring delta infection. A new source of delta antigen as a test reagent is, therefore, urgently required.

It is an object of the present invention to provide a method of 'unmasking' delta antigen or delta antigens (hereinafter referred to collectively as delta antigen) present in blood so that it becomes readily available for use as a diagnostic agent in the detection and determination of different classes of antibodies to the delta agent, including the IgM class of antibodies which are indicative of current infection.

DESCRIPTION OF THE PREFERRED EMBODIMENTS

According to a first aspect of the invention there is provided a process for unmasking delta antigen in the blood of an animal, known or caused to be infected with the antigen, so that it becomes readily detectable and available for participation in immunochemical reactions, said process comprising treating serum from the animal with a surfactant, the serum optionally being treated with an antibody-antigen dissociating agent.

The surfactant may be an anionic, cationic or non-ionic surfactant. The final concentration of the surfactant in the serum/surfactant mixture is determined by the particular surfactant used. A mixture of surfactants may also be used.

The surfactant is preferably a non-ionic surfactant. Especially preferred non-ionic surfactants are those manufactured by the Atlas Powder Company and marketed under the Trademark "TWEEN" and which are general purpose emulsifiers and surface active agents consisting of polyoxyethylene derivatives of sorbitan fatty acid esters or alkyl sorbitan polyoxyethylene. Tween 20 has been found to be particularly suitable in the process according to the invention. When Tween 20 is used, the final concentration of Tween 20 in the serum/surfactant mixture is preferably in the range 2–4% and optimally 3%. Other non-ionic surfactants which have been found to be particularly suitable in the process according to the invention are LUBROL PX, (marketed by Sigma London Chemical Co. Ltd.) NONIDET P40 (marketed by BDH Limited), TRITON X100 and TRITON X114 (marketed by Rohm and Haas Company) and TWEEN 60 and TWEEN 80, as hereinafter described. More generally the non-ionic surfactant may be any non-ionic surfactant used to separate surface protein or glycoprotein antigens from a virus. Triton X100E (Triton X100E is a Trade Mark) is conventionally used for that purpose and is an octylphenoxypolyethoxyethanol derived from the condensation of 9–10 moles of ethylene oxide with p-octylphenol. Another useful material is Triton N101 (Triton N101 is a Trade Mark) which is a nonylphenoxy-polyethoxyethanol comprising 9–10 ethoxy groups.

In general, those non-ionic surfactants that are condensates of ethylene oxide with fatty alcohols (Lubrol PX and the "Tween" series) tend to be more suitable and to give better results than the non-ionic surfactants that are condensates of ethylene oxide with aromatic alcohols (Nonidet P40 and the "Triton" series). Examples of suitable ionic surfactants are cetrimmonium bromide (CETRIMIDE) (cationic) and Sodium N-lauroylsarcosinate (anionic) as hereinafter described.

When it is desired to unmask delta antigen bound to anti-delta antibody in serum the latter is treated with an antibody-antigen dissociating agent in addition to a surfactant. Treatment with the dissociating agent precedes or is carried out simultaneously with the surfactant treatment. A preferred dissociating agent is potassium thiocyanate. Other suitable dissociating agents include, potassium bromide, potassium iodide, guanidine hydrochloride and urea.

Normally, the serum will be pooled from serum samples from a number of infected animals who have been found to have the delta antigen in their serum in reasonable quantities according to the methods hereinafter described.

Each constituent serum in the pool is first confirmed to contain the delta antigen by neutralisation of the delta antigen in competitive enzyme-immunoassay or radio-immunoassay with anti-delta antiserum so as to avoid false positive results.

Conveniently, one unit of delta antigen in the pool is defined as that amount of diluted pool in a 50 microlitre volume which will produce 2.1 times the optical density (measured at the wavelength appropriate to the chromogen being used) in an enzyme-immunoassay as hereinafter described, when compared with the optical density (measured at the same wavelength) produced by the same volume of pooled normal serum free of the delta antigen, or 2.1 times the counts per minute in a radio-immunoassay, when compared with the counts per minute produced by the same volume of pooled normal serum free of the delta antigen.

The animals are preferably primates or a rodent of the squirrel (sciuridae) family.

The primates are suitably human beings or chimpanzees.

Preferred squirrels are the ground-dwelling sciurids such as the marmots, which include the American woodchuck, chipmonks and prairie dogs. A preferred scuirid is the woodchuck marmota monax, also called the groundhog. Another suitable ground-dwelling squirrel is the beechy ground squirrel.

Hepatitis infection is endemic in woodchucks and it has been found that they are susceptible to the human delta antigen. It is possible that the delta infection in South America among persons who are not drug abusers referred to above could be attributable to transmission of the disease from lower animals.

According to a second aspect of the invention there is provided a method for the detection and determination of a component of the delta antigen-anti delta reaction, wherein the delta antigen is derived solely from blood, which comprises:
(a) adding a sample containing the component to be determined to an amount of one component of said delta antigen-anti-delta reaction in an insolubilized form;
(b) allowing the immunochemical reaction to take place;
(c) adding a predetermined amount of the antibody covalently linked to an enzyme or radio label; and
(d) determining the enzymatic or radiometric activity of the reaction medium, which is a measure of the amount of said component present in said added sample Preferably, the sample added is a serum sample.

When the component to be determined is the delta antigen, the serum is treated either before or after addition to the insolubilized form of the antibody with a surfactant as hereinabove described so as to unmask said delta antigen.

By "antigenically similar to primate delta antigen" is meant that injection of the delta antigen isolated from the lower animal into a primate such as chimpanzees provokes the appearance of primate anti-delta antibodies, namely antibody which will bind also to primate delta antigen.

Preferably the insolubilized form of the component of the delta antigen-anti-delta reaction comprises said component adsorbed on a surface adapted for protein adsorption.

Most preferably, the surface comprises a plastics microtitration plate or strip adapted for protein adsorption wherein the immunochemical reaction and the enzyme- or radio-immunoassay can take place. Especially suitable microtitration plates are gamma-irradiated microtitration plates. Examples of such gamma-irradiated microtitration plates are flat-well polystyrene microtitration plates marketed by DYNATECH under the trademark MICROELISA and those sold under the trademark "NUNC" IMMULON. Examples of strips are "Removawell" strips marketed by Dynatech.

When the insolubilized component is an anti-delta antibody, the surface is coated directly with an optimum dilution of anti-delta antibodies prepared by separating the immunoglobulin fraction of antiserum. It will be appreciated that the extent of dilution of the antiserum will depend on the amount of antibody present. In our studies we have found a dilution of 1/400 to 1/800 to be consistently suitable. One should endeavour to achieve a maximum dilution which is consistent which a reliable and reproducible result.

When the insolubilized component is the delta antigen, the surface is indirectly coated with the antigen via an intermediate layer of anti-delta anti-bodies bonded directly to said surface.

Preferably, the antibody-coated surface is incubated with serum containing the delta antigen, which serum may be treated before or after addition to the insolubilized form of the antibody with a surfactant and optionally a dissociating agent as hereinabove described.

Preferably, the enzyme of the antibody-enzyme conjugate is a peroxidase, especially horse radish peroxidase.

The radio label is preferably $^{125}$I.

The antibody is covalently linked to the enzyme or radio label in conventional manner as hereinafter described.

The anti-delta antibodies used for conjugation with the enzyme are preferably fractionated from serum by ion-exchange chromatography on DEAE cellulose.

According to a third aspect of the invention there is provided a test pack for the detection and determination of delta antigen in serum, which serum is treated with a surfactant and optionally an antibody-antigen dissociating agent to release the delta antigen, said test pack comprising:
(a) a given quantity of insolubilized anti-delta antibody or, alternatively, the necessary ingredients for preparing said insolubilized anti-delta antibody; and
(b) a corresponding given quantity of the coupling product of an enzyme or radio label with anti-delta antibody.

Preferably each test pack contains a sufficient amount of each of components (a) and (b) to carry out a number of tests.

The test pack preferably includes:
(c) a substrate for the determination of the activity of said enzyme when the test pack includes a coupling product of the enzyme with anti-delta antibody; and
(d) a given quantity of a surfactant and optionally a dissociating agent as hereinabove defined for unmasking of the delta antigen in a sample of said serum to be tested. Alternatively, the substrate or surfactant may be supplied by the user of the test pack.

The enzyme is preferably a peroxidase. An especially preferred peroxidase being horse radish peroxidase. The radio label is preferably $^{125}$I.

According to a fourth aspect of the invention there is provided a test pack for the detection and determination of anti-delta antibodies in serum which comprises:
(a') a given quantity of insolubilized delta antigen or, alternatively, the necessary ingredients for preparing said insolubilized delta antigen; and
(b') a corresponding given quantity of the coupling product of an enzyme or radio label with anti-delta antibody.

Preferably each test pack contains a sufficient quantity of each of components (a') and (b') to carry out a number of tests.

The test pack preferably includes:
(c') a substrate for the determination of the activity of said enzyme when the test pack includes a coupling product of the enzyme with anti-delta antibody.

The enzyme is preferably peroxidase. An especially preferred peroxidase is horse radish peroxidase. The radio label is preferably $^{125}$I.

The following Table—Table 1—gives the results of studies carried out to determined the optimum concentration of the various surfactants discussed above required to 'unmask' delta antigen in human serum according to the process of the invention.

TABLE I

| Surfactants used to 'unmask' delta antigen in human serum. | | | | |
|---|---|---|---|---|
| | | Concentration expressed as final concentration (%) | | |
| Surfactant | Type | Lower Limit | Upper Limit | Optimum |
| *TWEEN 20 | non-ionic | 2 | 4 | 3 |

TABLE I-continued

Surfactants used to 'unmask' delta antigen in human serum.

| Surfactant | Type | Concentration expressed as final concentration (%) | | |
|---|---|---|---|---|
| | | Lower Limit | Upper Limit | Optimum |
| TWEEN 60 | " | — | 0.3 | — |
| *TWEEN 80 | " | 0.3 | 4 | 3 |
| *LUNROL PX | " | 0.1 | 5 | 1 |
| NONIDET P40 | " | 0.3 | 3 | 0.3 |
| TRITON X100 | " | 0.3 | 4 | 0.3–3 |
| TRITON X114 | " | 0.3 | 2 | 0.3 |
| CETRIMIDE | cationic | 0.1 | >1 | 1 |
| Sodium N—Lauroyl sarcosinate | anionic | 0.3 | >1 | 1 |

* = particularly effective.

The invention will be further illustrated by the following Examples.

EXAMPLE 1

Detection of delta antigen in serum by enzyme-immunoassay (A) Anti-delta antibody-horse radish peroxidase conjugate preparation.

The anti-delta antibodies (IgG) used for conjugation were fractionated from serum by simple ion-exchange chromatography on DE52 DEAE cellulose marketed by Whatman Limited. The serum was passed through a column of DE52 and the aliquots corresponding to the first peak (measured at 254 nm) were collected and dialysed overnight against 0.02 M phosphate buffer; pH 8.0.

Conjugation with horse radish peroxidase (Sigma London Chemical Co. Ltd. Type VI) was carried out according to the anti-HBe conjunction method of Smith and Tedder, 1981 (J. Virol. Methods, 3, 1–11) except that anti-delta antibodies were used in place of anti-HBe, to give a conjugate with minimum non-specific binding properties.

(B) Preparation of the insolubilized anti-delta antibody —'Solid Phase'.

MICROELISA flat-well polystyrene microtitration plates were coated with 75 µl of a 1/800 dilution of anti-delta antibodies. The anti-delta antibody was prepared by separating the immunoglobulin fraction of serum with 40% ammonium sulphate. The separation step was carried out twice and each time the resultant immunoglobulin precipitate was dissolved in 0.02 M tris buffer; pH 7.6, containing 0.1% sodium azide as a preservative. This buffer will hereinafter be referred to as the coating buffer.

The plates were allowed to stand overnight at room temperature (approximately 20° C.) and were then washed at least three times with coating buffer and then 'quenched' by filling the wells with a quantity of 1% bovine serum albumin coating buffer. The plates containing a small amount of the bovine serum albumin solution were stored at approximately 4° C.

(C) Detection of delta antigen by enzyme-immunoassay

50 µl serum samples (prepared in conventional manner by centrifugation of clotted blood) to be tested for delta antigen were placed in the solid phase wells prepared under B) above. To each well was added 25 µl of Tween 20 (BDH) diluted with 0.15 M phosphate buffered saline (PBS); pH 7.2 so as to achieve a final concentration of 3% in the well. The plates were incubated overnight at room temperature (approximately 20° C.) and then washed five times with PBS containing 0.05% Tween 20 (PBS-Tween).

75 µl of the horse radish peroxidase conjugated anti-delta diluted 1/800 with PBS containing 5% rabbit normal serum and 5% normal human serum was added to each well and the plate incubated at 37° C. for two hours. The presence of the rabbit and human normal serum provides a protein source which prevents non-specific sticking of the conjugate to the solid phase. The 1/800 dilution of the conjugate was found to give maximum sensitivity in a checkerboard titration. 50% calf serum may be used in place of the 5% rabbit serum and 5% normal human serum.

After incubation at 37° C. for two hours, the wells were washed four times with PBS-Tween and incubated with 75 µl of enzyme substrate. The enzyme substrate was prepared by dissolving 8 mg of 2,2-azino-di-(3-ethylbenzthiazoline sulphonic acid) (ABTS) (Sigma) in 10 ml of 0.5 M citrate phosphate buffer at a pH of between 4.0 and 4.1 to which 20 µl of 100 vol. hydrogen peroxide (Analar quality) were added.

After 30 minutes incubation in the dark at room temperature (approximately 20° C.) the reaction was stopped with 50 µl of 0.2 M sodium fluoride (Sigma) in PBS. The optical density of each well was measured at either 650 or 410 nm. in a Dynatech Microelisa mini-reader MR 950.

As substrate/chromogen one may also use 75 µl of a solution of hydrogen peroxide/o-phenylene diamine (OPD) prepared by dissolving 10 mg OPD in 10 ml 0.5 M citrate Phosphate buffer at pH 5.5 and adding 5 µl of 100 vol. hydrogen Peroxide. The stopping solution for $H_2O_2$/OPD is suitably IN $H_2SO_4$. Optical density is measured at 490 nm.

Each batch of tests included a minimum of six negative controls consisting of normal human serum (three unit pool, each unit negative for all HBV markers) and two positive controls consisting of serum from the delta antigen pool.

A serum sample is considered positive for delta antigen if it repeatedly gives an optical density of greater than 2, and especially greater than 2.5, times the mean optical density of the negative control and is neutralisable in a blocking assay, as hereinafter described, with anti-delta antibodies.

EXAMPLE 2

Blocking Assay for the Confirmation of Delta Antigen Positives.

A blocking assay for the confirmation of delta antigen positive sera was carried out as in the case of Example 1 except that in the first stage, i.e., prior to the addition of antibody-enzyme conjugate positive samples were incubated with 20 µl of a high-titre anti-delta positive serum and Tween 20 simultaneously. Accordingly, it will be appreciated that no antigen was available for reaction with the enzyme-conjugated antibody upon addition of same.

EXAMPLE 3

Use of Serum Derived Delta Antigen in the Detection of Anti-Delta Antibodies by enzyme-immunoassay.

The solid phase wells prepared as in Example 1 B) were incubated overnight at room temperature (approximately 20° C.) with 75 µl of delta antigen pool serum diluted with PBS buffered Tween 20 so as to achieve a final concentration of 3% Tween 20 and containing one unit of delta antigen. After incubation overnight at room temperature the wells were washed five times with PBS Tween. A 25μl sample of neat serum to be tested for anti-delta antibodies was added to each well followed by 50μl of PBS and the wells were then incubated for 2 hours at 37° C. The wells were then washed four times with PBS Tween. Whereupon 75 μl antibody-enzyme conjugate was added to each well. The conjugate was diluted with PBS containing 5% rabbit serum and 5% normal human serum as described above so as to give a maximum positive/negative optical density ratio. The wells were then further incubated for two hours at 37° C. Washing, substrate addition, stopping and reading of the wells was carried out as in the case of Example 1 above.

A specimen was considered positive for anti-delta if it repeatedly reduced the difference between the mean optical densities of three delta antigen and six normal serum controls by 50% or more.

Using the above method it was possible to obtain a yield of between 800 and 2400 anti-delta tests per 10 ml of delta antigen positive serum.

EXAMPLE 4

Specificity Tests

Since the anti-delta conjugate contained anti-HBc HRPO and anti-HBe HRPO it was necessary to exclude reactions in the assay with 'e' and core, particularly since detergent treatment removes surface antigen from Dane particles (Almeida et al (1971) Lancet, ii, 1225-1227) and can enhance 'e' antigen in serum (Shattock, A. G. 1979 thesis "Studies on Hepatitis B with particular reference to Hepatitis B 'e' antigen", Library University College Dublin). Tests were therefore carried out with anti-HBe and anti-HBc in place of anti-delta in the blocking assay for confirmation of delta antigen positives. The test methods were also carried out substituting anti-HBe HRPO, prepared by the same method, and anti-HBc HRPO (Abbott Labs) in place of the anti-delta HRPO. Tests for delta antigen were also carried out on a high titre (1/32 by immunodiffusion) HBsAg positive serum where virtually all of the hepatitis B particles were shown by microscopy to be Dane particles, and also on 20 sera strongly positive for rheumatoid factor. Anti-delta HRPO was also substituted in an identical HBeAg test.

RESULTS

The delta antigen pools and Sera positive in the delta antigen test were not neutralised by anti-HBe or anti-HBc. When the anti-delta HRPO, diluted as in the delta antigen test, was substituted for anti-HBe HRPO in an otherwise identical test for HBeAg it failed to detect any of a small panel of strong and weak HBeAg positive sera. Similarly all tests were negative when anti-HBc HRPO (Abbott Labs.) was substituted for anti-delta HRPO in the delta antigen test.

All 20 strong rheumatoid factor positive sera were negative in the delta antigen test.

EXAMPLE 5

Use of Serum-Derived Delta Antigen in the Detection of IgM Class Antibodies to Delta Antigen by enzyme immunoassay Samples to be tested and four normal human serum controls were diluted between 1/10 and 1/800, depending on the sensitivity required, in PBS Tween containing 2% rabbit or 5% calf serum. A 1/600 dilution was routinely found to be most suitable.

Duplicate 50 μl volumes of the dilution selected were incubated with a solid phase consisting of Dynatech MICROELISA plates coated with rabbit anti-human IgM μ chain specific antiserum (Dako Limited). The wells were then washed with PBS Tween five times and incubated overnight at room temperature with one unit of delta antigen pool containing 3% final concentration of Tween 20 in one of each pair of duplicate wells, and 50 μl of normal human serum diluted, as in the case of the delta antigen pool, to contain a final concentration of 3% Tween 20, in the duplicate well. Washing, conjugate addition, substrate addition, stopping and reading were carried out as in the case of Example 1.

A specimen is considered positive for the IgM class of anti-delta antibody if its optical density is more than twice that of the mean negative controls and negative in the sample control well with normal human serum in place of delta antigen.

Determination of IgM class antibodies to delta antigen gives an indication of the stage of infection, since IgM class antibodies appear only in the early and active stages of infection with delta antigen. Accordingly, the presence of IgM class antibodies will give an indication that infection is recent or current and is indicative of ongoing replication of the delta agent.

EXAMPLE 6

Release of delta antigen from delta antibody 1.75 ml of 4M potassium thiocyanate was added to a 250 μl sample of serum to be tested. The serum-potassium thiocyanate mixture was centrifuged at 37,000 g for 90 minutes in a Beckmann Model L ultracentrifuge with type 50 angle rotor. The supernatant was carefully removed and the pellet resuspended in 100 μl of PBS. The resuspended pellet and supernatant were then dialysed three times in a Minicon A25 microsolute concentrator cell (Minicon is a Trade Mark of Amicon Corporation) to a final volume of 200 μl. The dialysed products were treated with Tween 20 and tested for delta antigen according to Example 1 C).

EXAMPLE 7

(A) Detection of delta antigen in serum by radio-immunoassay.

Preparation of labelled anti-delta conjugate

Fractionation of anti-delta for radioactive labelling was carried out as in Example 1 A). Radiolabelling with $^{125}$Iodine was carried out using Bolton and Hunter reagent (Amersham International Ltd.) in accordance with the manufacturers' instructions.

(B) Preparation of the insolubilized anti-delta antibody 'Solid Phase'.

Removawell strips (Dynatech Ltd.) were coated with 75 μl of a suitable (1/2000) dilution of anti-delta antibody prepared as in Example 1 B).

Alternatively 6.4 mm specular finished polystyrene beads (Northumbria Biologicals Ltd.) were coated and stored in a suitable dilution (1/2000) of the same anti-delta preparation. Dilution of the anti-delta preparation was in Tris azide buffer as in Example 1 B).

Strips and beads were washed three times in PBS Tween before use.

(C) Detection of delta antigen

50 μl serum samples to be tested for delta antigen were placed in the wells of solid phase strips prepared as above in B). To each well was added 25 μl of Tween 20 (BDH) diluted with PBS so as to achieve a final concentration of 3% in the well. The strips were incubated overnight at room temperature (approx. 20° C.) and then washed five times with PBS-Tween.

75 μl of $^{125}$I-labelled anti-delta, containing approximately 25 nCi$^{125}$I, in coating buffer containing 2% BSA and 20% normal human serum, was added to each well and incubated at 37° C. for 2 hours. The wells were washed five times with PBS Tween and each well was cut off and counted in an Abbott Autologic 201 gamma-counter with automatic background subtraction. In place of 20% normal human serum, one may use 50% calf serum.

A sample was considered positive for delta antigen if the counts exceeded those of the mean of six normal human serum controls, by a factor of 2.1 or more.

Confirmation of positives was by demonstrating a greater than 50% reduction in counts when 10 μl of a standard high-titre anti-delta serum was added to the test serum compared to the same serum without added anti-delta, in a blocking assay.

The assay with beads as solid phase was carried out in the same manner as described under (C) above but with the beads held in reaction trays (Abbott Labs.) and the reagent volume increased to 200 μl.

EXAMPLE 8

Use of serum derived delta antigen in the detection of anti-delta antibodies by radio-immunoassay The solid phase strips prepared as in Example 7 were incubated overnight with 75 μl of delta antigen pooled serum diluted with PBS-Tween so as to achieve a final concentration of 3% Tween 20 and containing a minimum of one unit of delta antigen. After incubation overnight at room temperature the wells were washed five times with PBS-Tween. A 25 μl sample of neat serum to be tested for anti-delta antibodies was added to the well followed by 50 1 PBS and the wells were incubated for 2 hours at 37° C. The wells were then washed four times with PBS-Tween. Addition of radio-labelled anti-delta, washing and counting were carried out as in Example 7 (delta antigen test).

A sample was considered positive if it repeatedly reduced the counts of the mean of four normal human serum control samples by 50% or more.

EXAMPLE 9

Use of serum-derived delta antigen in the detection of IgM class antibodies to delta antigen by radio-immunoassay Samples to be tested and four normal human serum controls were diluted between 1/10 and 1/800 (1/600 was found best routinely) depending on the sensitivity required, in PBS-Tween containing 2% rabbit serum. 5% foetal calf serum may also be used.

Duplicate 50 μl volumes of the dilution selected were incubated overnight at 4° C. with a solid phase consisting of Removawell (Dynatech Ltd.) strips coated with rabbit anti-human μ chain specific antiserum (Dako Ltd.) diluted 1/400 in 50 mM carbonate buffer pH 9.6 overnight at 4° C.

The wells were then washed five times with PBS-Tween and incubated overnight at room temperature with one unit of delta antigen pool containing 3% final concentration of Tween 20 in one of each pair of duplicate wells, and 50 μl of normal human serum diluted as in the case of the delta antigen pool, to contain a final concentration of 3% Tween 20, in the duplicate well. Washing, addition of radio labelled anti-delta conjugate, washing and counting were carried out as before in Examples 7 and 8.

A specimen was considered postive for the IgM class of anti-delta if its counts were more than 2.1 times that of the mean negative controls and negative in the sample control well with normal human serum in place of delta antigen.

Alternatively the above procedure can be carried out as described but using polystyrene beads coated with the same rabbit anti-human μ chain antiserum in reaction trays (Abbott Labs) and increasing the reagent volumes to 200 μl.

EXAMPLE 10

Method of detecting delta antigen using combined surfactant and dissociating agent treatment.

An extraction mixture for extracting delta antigen from serum was prepared as follows: 1 volume of 6M potassium thiocyanate was slowly added to 2 volumes of normal human serum. Neat Tween 20 was then added to give a final concentration in the mixture of 9%. This extraction mixture was used as a stock medium in detection assays for delta antigen by enzyme-immunoassay and radio-immunoassay according to Example Nos. 1C and 7C, respectively, except that 25 μl of extraction mixture was substituted for 25 μl of 9% buffered Tween 20. The final concentration of Tween 20 in each well was 3% as in the case of Example Nos. 1C and 7C.

EXAMPLE 11

Method of detecting anti-delta antibodies, including IgM class antibodies, using delta antigen derived from serum by combined surfactant and dissociating agent treatment.

The detection methods of Example Nos. 3, 5, 8 and 9 were repeated except that the delta antigen used in coating the anti-delta solid phase was diluted in an extraction medium prepared by slowly adding 1 volume of 2M potassium thiocyanate to 2 volumes of normal human serum with mixing and then adding Tween 20 so as to achieve a concentration of Tween 20 in the final mixture of 3%.

With this method it was possible to obtain a yield of up to 50,000 anti-delta tests per 10 ml of delta antigen positive serum.

EXAMPLE 12

Isolation of delta antigen from woodchuck serum. Marmota monax species of woodchuck were inoculated with human HBsAg positive serum containing delta antigen. Six weeks after inoculation serum from these animals was inoculated into a second set of woodchucks. Samples of blood from this second set were tested for delta antigen according to Example 1. When the delta antigen appeared to have reached a peak level, the animals were sacrificed and the serum separated from the blood by conventional centrifugation techniques.

EXAMPLE 13

Test for human anti-delta using serum derived woodchuck delta antigen.

Examples 3 and 5 were repeated except that solid phase wells prepared as in Example 1 B) were incubated with 50 μl aliquots of woodchuck serum in place of human serum.

EXAMPLE 14

Examples 8 and 9 were repeated except that solid phase wells prepared as in Example 7B) were incubated with 50 μl aliquots of woodchuck serum in place of human serum. Table 2 gives the results of tests carried out on blood samples collected from 217 drug-abusers in Dublin at the Drug Treatment and Advisory Centre, Jervis Street Hospital, Dublin, with initially diagnosed acute hepatitis (HBsAg positive), to determine the presence of delta antigen and delta antibody according to the method of the invention. The samples were collected over a period of 18 months and stored by freezing. The delta antigen obtained from blood has been found to be very stable since it can withstand freezing over a considerable period of time as the present studies have shown.

TABLE 2

Determination of delta antigen and delta antibodies in Dublin drug-abusers with initially diagnosed acute hepatitis

| Total tested for delta/anti-delta | | Total delta positive | |
|---|---|---|---|
| 217 | | 75 (35%) | |
| Total delta positive | Total delta antigen | Total anti-delta only | Total sero-conversion |
| 75 | 53 (71%) | 22 (29%) | 14 (19%) |

Table 2 shows that 75 (35%) of the 217 drug-abusers tested had delta markers. It will be observed that of the 75 found to be delta positive 71% (53) were found to have delta antigen in their serum which is significant in the light of previous findings which have shown that the delta antigen is found to occur only occasionally and transiently (a few days) in the blood of infected humans. In the latter 53 drug abusers, delta antigenaemia was demonstrated in the acute phase sera for a maximum of 14 days. Anti-delta without prior delta antigenaemia being detected, was found in 22 (29%) of those tested. Using the process, method and test packs according to the invention, it is possible to detect delta antigen for up to 10–14 days of the acute stage of infection, and anti-delta during convalescence and for months or years afterwards.

The following Table—Table 3—gives the results of a double-blind comparison test comparing the radio-immunoassay technique of Rizzetto et al supra with the enzyme immunoassay technique according to the invention for the determination of delta antigen and anti-delta:

TABLE 3

Double-Blind Comparison

| Sera Type | No. of Samples | Test Procedure Invention EIA | RIA test (Rizzetto) |
|---|---|---|---|
| Negative for both delta Ag and Ab | 14 | 14 | 14 |
| Delta Ag positive | 17 | 12 strong 5 weak | 12 strong 0 weak |
| Anti-delta positive | 16 | 7 strong 9 weak | 7 strong 0 weak |

The sera shown to be positive for delta antigen according to the method of the invention have been repeatedly confirmed by blocking assays following the procedure of Example 2 above. It is important to note that all but one of the nine weak anti-delta positives had delta antigenaemia at the start of their illness. It would appear, therefore, from the results given in Table 3 that the antibody detection method according to the invention may be more sensitive for the detection of anti-delta than the hitherto used method of Rizzetto et al. This result is unexpected.

A similar result was obtained of anti-delta sensitivity on a double-blind comparison with another radio-immunoassay using liver antigen, carried out by Hansson, B., Malmo, Sweden as shown in Table 4.

It would appear also that the serum-derived delta antigen used in the method according to the invention is more suitable for the detection and determination of serum delta antibodies than the liver-derived antigen used by Rizzetto et al and Hansson. It is likely that the milder treatment using surfactants according to the process of the invention is responsible for the increased and unexpected sensitivity of the antigen and antibody detection methods according to the invention.

TABLE 4

Double Blind Comparison

| Sample No. | TEST PROCEDURE Anti-delta (% blocking) (Hansson) | Invention (% blocking) |
|---|---|---|
| 1 | ±(65,40) | — |
| 2 | +(92) | +(87) |
| 3 | +(75) | +(86) |
| 4 | — | — |
| 5 | +(75) | +(97) |
| 6 | — | — |
| 7 | — | +(64) |
| 8 | — | — |
| 9 | — | — |
| 10 | — | +(61) |
| 11 | +(97) | +(64) |
| 12 | — | — |
| 13 | — | — |
| 14 | — | +(51) |
| 15 | +(72) | +(84) |
| 16 | — | — |
| 17 | +(73) | +(84) |
| 18 | +(85) | +(87) |
| 19 | — | — |
| 20 | +(56,59) | +(87) |
| 21 | — | — |
| 22 | +(91) | +(97) |
| 23 | — | +(69) |
| 24 | — | — |
| 25 | +(89) | +(90) |
| 26 | — | +(58) |
| 27 | — | — |
| 28 | — | — |
| 29 | — | +(70) |
| 30 | +(73) | +(97) |
| 31 | — | — |
| 32 | — | — |
| 33 | +(89) | +(87) |

TABLE 4-continued

| | Double Blind Comparison | |
|---|---|---|
| | TEST PROCEDURE | |
| Sample No. | Anti-delta (% blocking) (Hansson) | Invention (% blocking) |
| 34 | — | +(71) |
| TOTAL | 12 | 19 |

The present invention establishes that blood can be readily used as a source of antigen in a technique for the detection of anti-delta antibodies if it is treated in accordance with the process according to the invention described above. The present invention obviates the necessity for isolating delta antigen from liver as a source of antigen for the detection and determination of anti-delta antibodies. Many laboratories have been unable to undertake delta testing because of the reluctance of pathologists to carry out post-mortems on drug-abusers who have died from hepatitis in order to obtain liver for the extraction of delta antigen according to the procedure of Rizzetto et al 1980 (J. Immunol. 125, 318–324) which is the sole procedure used at present for obtaining a source of delta antigen. The present invention demonstrates that there is an alternative source of delta antigen for delta testing. The use of serum delta antigen according to the invention is not only practical, with a yield of up to 50,000 anti-delta tests per 10 ml of delta antigen positive serum, but is also specific and has a sensitivity which is at least comparable with that of the known techniques using liver-derived delta antigen. The invention provides reproducible enzyme-immunoassay (ELISA) and radio-immunoassay (RIA) techniques for the detection of acute phase serum delta antigen and anti-delta of IgG and IgM classes using serum as the source of delta antigen. These techniques are specific and very sensitive.

Although not wishing to be bound by any theoretical explanation of the invention we believe that the surfactant employed in the process according to the invention unmasks the delta antigen by removing HBsAg protein associated therewith, thereby revealing a core corresponding to the delta antigen proper. It is known that certain non-ionic surfactants strip off HBsAg from HB virus so as to release the core (Almeida, J. D. et al, The Lancet December 4, 1971). It is also likely that the surfactant treatment releases delta antigen bound to plasma protein as discussed above.

We claim:

1. A process for obtaining delta antigen from an animal, known or caused to be infected with the antigen, for use as a source of delta antigen for diagnostic assays, said process comprising treating blood serum from the animal with a predetermined amount of a surfactant selected from the group consisting of condensates of ethylene oxide with fatty alcohols, condensates of ethylene oxide with aromatic alcohols, cetrimonium bromide and sodium N-lauroyl sarcosinate.

2. A process according to claim 1, wherein the surfactant is a condensate of ethylene oxide with a fatty alcohol.

3. A process according to claim 1, wherein the serum is treated with an antibody-antigen dissociating agent to unmask or release delta antigen bound to anti-delta antibody, the dissociating agent being selected from the group consisting of potassium thiocyanate, potassium bromide, potassium iodide, guanidine hydrochloride and urea, any of said dissociating agents being suitable for use with any one of said surfactants.

4. A process according to claim 3, wherein the treatment with the dissociating agent is carried out simultaneously with the surfactant treatment.

5. A process according to claim 4, wherein the serum is obtained from a primate.

6. A process according to claim 5, wherein the primate is a human.

7. A process according to claim 6, wherein the serum is obtained from a rodent of the sciuridae family.

8. A process according to claim 7, wherein the sciurid is marmota monax.

9. An immunoassay method for the detection and determination of the delta antigen component or the anti-delta component of a delta antigen-anti-delta reaction in a body fluid, wherein the delta antigen is derived solely from blood, which comprises:
(a) adding a sample of the body fluid containing the component to be determined to an amount of the other component of said delta antigen-anti-delta reaction in an insolubilized form;
(b) allowing an immunochemical reaction to take place between said components to form a delta antigen-anti-delta reaction product;
(c) adding a predetermined amount of labelled antibody which is anti-delta antibody covalently linked to an enzyme or radio label; and
(d) determining the enzymatic or radiometric activity of the reaction medium, which is a measure of the amount of said component present in said sample of the body fluid.

10. A method according to claim 9, wherein the sample is a serum sample.

11. A method according to claim 9, for the determination of delta antigen wherein the serum is treated before or after addition to the insolubilized form of the antibody with a predetermined amount of a surfactant selected from the group consisting of condensates of ethylene oxide with fatty alcohols, condensates of ethylene oxide with aromatic alcohols, cetrimonium bromide and sodium N-lauroyl sarcosinate.

12. A method according to claim 11, wherein the serum is further treated, before, simultaneously or after treatment with the surfactant, with an antibody-antigen dissociating agent to unmask or release delta antigen bound to anti-delta antibody; the dissociating agent being selected from the group consisting of potassium thiocyanate, potassium bromide, potassium iodide, guanidine hydrochloride and urea, any of said dissociating agents being suitable for use with any one of said surfactants.

13. A method according to claim 9, wherein the insolubilized form of the component of the delta antigen-anti-delta reaction comprises said component adsorbed on a protein-adsorbing surface.

14. A method according to claim 13, wherein the surface comprises a protein-adsorbing plastics microtitration plate or strip.

15. A method according to claim 13, for the determination of delta antigen, wherein the surface is coated directly with an optimum dilution of anti-delta antibodies prepared by separating the immunoglobulin fraction of antiserum.

16. A method according to claim 13, for the determination of anti-delta antibodies, wherein the surface is indirectly coated with delta antigen by an intermediate layer of anti-delta antibodies bonded directly to said surface.

17. A method according to claim 16, wherein the antibody-coated surface is incubated with serum containing the delta antigen, said serum being treated before or after addition to the insolubilized form of the antibody with a surfactant selected from the group consisting of condensates of ethylene oxide with fatty alcohols, condensates of ethylene oxide with aromatic alcohols, cetrimonium bromide and sodium N-lauroyl sarcosinate.

18. A method according to claim 11, wherein the serum is further treated, before, simultaneously or after treatment with the surfactant, with an antibody-antigen dissociating agent to unmask or release delta antigen bound to anti-delta antibody, the dissociating agent being selected from the group consisting of potassium thiocyanate, potassium bromide, potassium iodide, guanidine hydrochloride and urea, any of said dissociating agents being suitable for use with any one of said surfactants.

19. A method according to claim 4, wherein said labelled antibody is labelled with the enzyme horse radish peroxidase.

20. A method according to claim 4, wherein said labelled antibody is labelled with the radio label is $^{125}I$.

21. A test pack for the detection and determination of delta antigen in serum by immunoassay comprising:
    (a) a bottle or vial containing a buffered surfactant solution for unmasking or releasing the delta antigen in the serum, the surfactant being selected from the group consisting of condensates of ethylene oxide with fatty alcohols, condensates of ethylene oxide with aromatic alcohols, cetrimonium bromide and sodium N-lauroyl sarcosinate;
    (b) one or more microtitration plate(s) or strip(s) coated with a given quantity of insolubilized anti-delta antibody; and
    (c) a bottle or vial containing a corresponding coupling product of an enzyme or radio label with anti-delta antibody.

22. A test pack according to claim 21, wherein the buffered surfactant solution additionally contains an antibody-antigen dissociating agent selected from the group consisting of potassium thiocyanate, potassium bromide, guanidine hydrochloride and urea, any of said dissociating agents being suitable for use with any one of said surfactants.

23. A test pack for the detection and determination of delta antigen in serum by immunoassay comprising:
    (a) a bottle or vial containing a buffered surfactant solution for unmasking or releasing the delta antigen in the serum, the surfactant being selected from the group consisting of condensates of ethylene oxide with fatty alcohols, condensates of ethylene oxide with aromatic alcohols, cetrimonium bromide and sodium N-lauroyl sarcosinate;
    (b) one or more microtitration plate(s) or strip(s) coated with a given quantity of insolubilized anti-delta antibody;
    (c) a bottle or vial containing an antibody-antigen dissociating agent selected from the group consisting of potassium thiocyanate, potassium bromide, potassium iodide, guanidine hydrochloride and urea, any of said dissociating agents being suitable for use with any one of said surfactants; and
    (d) a bottle or vial containing a corresponding given quantity of the coupling product of an enzyme or radio label with anti-delta antibody.

24. A test pack according to claim 22, which includes a bottle or vial containing a substrate for the determination of the activity of said enzyme when the test pack contains a coupling product of the enzyme with anti-delta antibody.

25. A test pack according to claim 23, which includes a bottle or vial containing a substrate for the determination of the activity of the said enzyme when the test pack contains a coupling product of the enzyme with anti-delta antibody.

26. A test pack according to claim 24, wherein the enzyme is horse radish peroxidase.

27. A test pack according to claim 25, wherein the enzyme is horse radish peroxidase.

28. A test pack according to claim 21, wherein the radio label is $^{125}I$.

29. A test pack for the detection and determination of anti-delta antibodies in serum by immunoassay which comprises:
    (a) one or more microtitration plate(s) or strip(s) coated with a given quantity of insolubilized delta antigen, the delta antigen having been derived solely from blood; and
    (b) a bottle or vial containing a corresponding quantity of the coupling product of an enzyme or radio label with anti-delta antibody.

30. A test pack for the detection and determination of anti-delta antibodies in serum by immunoassay which comprises:
    (a) one or more microtitration plate(s) or strip(s) coated with a given quantity of insolubilized anti-delta antibody;
    (b) a bottle or vial containing serum delta antigen;
    (c) a bottle or vial containing a buffered surfactant solution for unmasking or releasing the delta antigen in the serum, the surfactant being selected from the group consisting of condensates of ethylene oxide with fatty alcohols, condensates of ethylene oxide with aromatic alcohols, cetrimonium bromide and sodium N-lauroyl sarcosinate; and
    (d) a bottle or vial of a corresponding quantity of the coupling product of an enzyme or radio label with anti-delta antibody.

31. A test pack according to claim 30, wherein the buffered surfactant solution additionally contains an antibody-antigen dissociating agent selected from the group consisting of potassium thiocyanate, potassium bromide, potassium iodide, guanidine hydrochloride and urea, any of said dissociating agents being suitable for use with any one of said surfactants.

32. A test pack for the detection and determination of anti-delta antibodies in serum by immunoassay which comprises:
    (a) one or more microtitration plate(s) or strip(s) coated with a given quantity of insolubilized anti-delta antibody;
    (b) a bottle or vial containing serum delta antigen;
    (c) a bottle or vial containing a buffered surfactant solution for unmasking or releasing the delta antigen in the serum, the surfactant being selected from the group consisting of condensates of ethylene oxide with fatty alcohols, condensates of ethylene oxide with aromatic alcohols, cetrimonium bromide and sodium N-lauroyl sarcosinate; and (d) a bottle or vial containing an antibody-antigen dissociating agent selected from the group consisting of potassium thiocyanate, potassium bromide, potassium iodide, quanidine hydrochloride and urea, any of said dissociating agents being suitable for use with any one of said surfactants.

33. A test pack according to claim 29, which includes a bottle or vial containing a substrate for the determination of the activity of said enzyme when the test pack contains a coupling product of the enzyme with anti-delta antibody.

34. A test pack according to claim 33, which includes a bottle or vial containing a substrate for the determination of the activity of said enzyme when the test pack contains a coupling product of the enzyme with anti-delta antibody.

35. A test pack according to claim 31, which includes a bottle or vial containing a substrate for the determination of the activity of said enzyme when the test pack contains a coupling product of the enzyme with anti-delta antibody.

36. A test pack according to claim 32, which includes a bottle or vial containing a substrate for the determination of the activity of said enzyme when the test pack contains a coupling product of the enzyme with anti-delta antibody.

37. A test pack according to claim 33, wherein the enzyme is horse radish peroxidase.

38. A test pack according to claim 34, wherein the enzyme is horse radish peroxidase.

39. A test pack according to claim 35, wherein the enzyme is horse radish peroxidase.

40. A test pack according to claim 36, wherein the enzyme is horse radish peroxidase.

41. A test pack according to claim 29, wherein the radio label is $^{125}I$.

* * * * *